United States Patent [19]

Mathiaparanam

[11] Patent Number: 5,200,519

[45] Date of Patent: Apr. 6, 1993

[54] MONO(INDOLYLETHYLENYL)PHTHA-LIDES
[75] Inventor: Ponnampalam Mathiaparanam, Appleton, Wis.
[73] Assignee: Appleton Papers Inc., Appleton, Wis.
[21] Appl. No.: 817,263
[22] Filed: Jan. 3, 1992
[51] Int. Cl.$^5$ ................ C07D 405/06; C07D 405/14; C07D 413/14
[52] U.S. Cl. .................... 544/144; 544/143; 546/165; 546/94; 548/427; 548/456
[58] Field of Search ............... 544/143, 144; 546/165, 546/94; 548/427, 456

[56] References Cited
U.S. PATENT DOCUMENTS
4,970,308 11/1990 Mathiaparanam ............... 548/456

Primary Examiner—Robert W. Ramsuer
Attorney, Agent, or Firm—Benjamin Mielilis

[57] ABSTRACT

Preparation of novel mono(indolylethylenyl) phthalides is disclosed. Specifically, these compounds are chromogenic mono(indolylethylenyl)phthalides of the formula

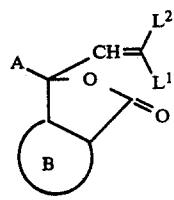

wherein A is as hereinafter defined and selected from moieties of the type

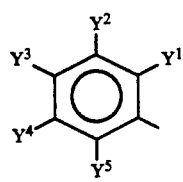

-continued

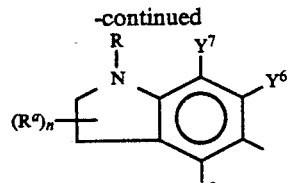

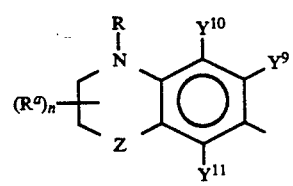

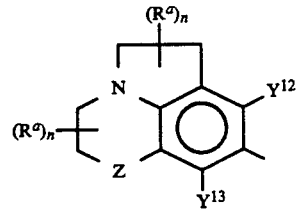

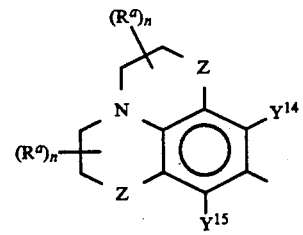

wherein L is an indole moiety as hereinafter defined; wherein B is a moiety of the type

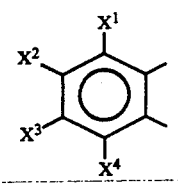

as hereinafter defined. The process disclosed comprises condensing indolylethylene with a keto acid or its derivative and an electron acceptor in an organic solvent.

11 Claims, 2 Drawing Sheets

MONO(INDOLYLETHYLENYL)PHTHALIDES

FIELD OF THE INVENTION

Background of the Invention

This invention relates to chromogenic mono(indolylethylenyl)phthalides (I) and methods for their production. More particularly, this invention relates to chromogenic compounds that are colorless or light-colored initially but provide intense colors when reacted with an electron accepting coreactant material; and, therefore, are eligible for use in pressure sensitive recording systems and thermal recording systems that can be read by a machine capable of reading in the wavelength range of 400 to 900 nm.

The chromogenic compounds of this kind also find use in photosensitive printing materials, typewriter ribbons, inks and the like. Imaging or printing in desired areas on support webs or sheets may be accomplished by effecting localized reactive contact between chromogenic material and an electron accepting material on or in such web or sheet, such material being brought thereto by transfer or originally there in situ. This selective reactive contact forms the colored prints or images in the intended areas.

The colorable chromogenic compounds of the invention can be combined with other chromogenic materials covering other or wider spectral ranges and can be used in pressure sensitive and thermal recording systems to provide images or prints which absorb over wider ranges of the electromagnetic spectrum. The commercial significance is that a larger assortment of available optical or near infrared readers can thus be effectively useful with record systems incorporating the chromogenic compounds of the invention.

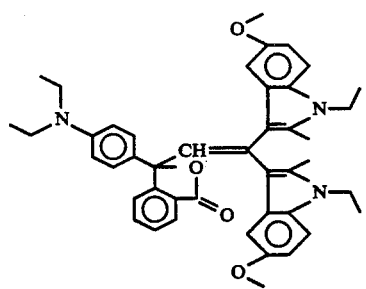

3-[1,1-bis(1-ethyl-5-methoxy-2-methylindole-3-yl)ethylene-2-yl]-3-(4-diethylaminophenyl)phthalide.

Figure 2:
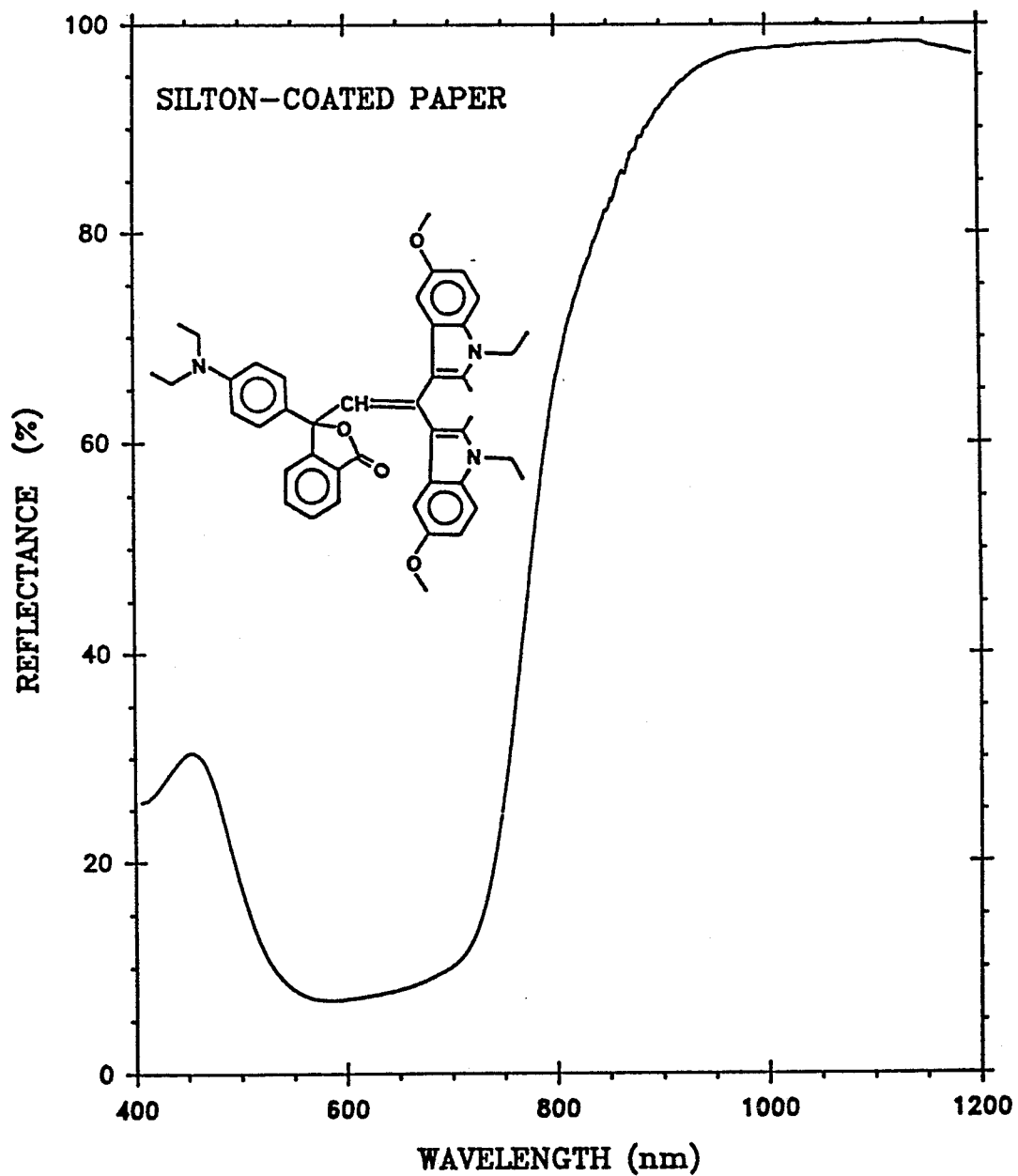

FIG. 2 is a graph of reflectance of the above compound when coated on silton-coated paper. Example 1 details the synthesis of this compound.

DETAILED DESCRIPTION

The chromogenic compounds of this invention have the following general formula:

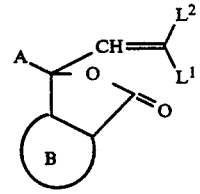
(I)

wherein A is independently selected from

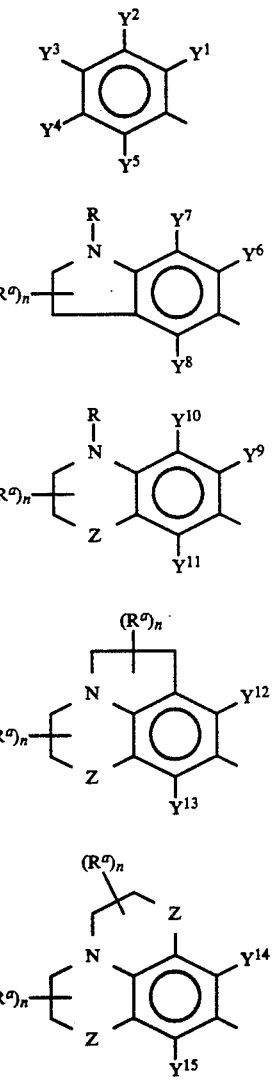

wherein $Y^3$ is independently selected from dialkylamino including symmetrical and unsymmetrical alkyl ($C_1$–$C_8$), alkylcycloalkylamino, dicycloalkylamino, alkylarylamino, diarylamino, dialkoxyalkylamino,

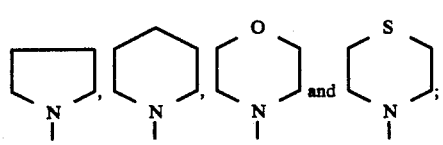

wherein each of $Y^1$, $Y^2$, $Y^4$-$Y^{15}$ is the same as $Y^3$ or independently selected from alkyl ($C_1$-$C_8$), alkoxy ($C_1$-$C_8$) or halogen;

wherein R is independently selected from alkyl ($C_1$-$C_8$), alkoxyalkyl, aryl (substituted or unsubstituted);

wherein Z is independently selected from $CH_2$, O, S, $SO_2$ or NR.

wherein each $R^a$ is independently selected from alkyl ($C_1$-$C_8$) and hydrogen;

wherein each n is an integer selected from 0 to four;

wherein B is independently selected from

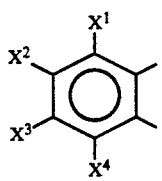

wherein each of $X^1$-$X^4$ is independently selected from hydrogen, halogen, alkyl ($C_1$-$C_8$), alkoxy ($C_1$-$C_8$), dialkylamino including symmetrical and unsymmetrical alkyl ($C_1$-$C_8$), alkylcycloalkylamino, dicycloalkylamino, alkylarylamino, diarylamino,

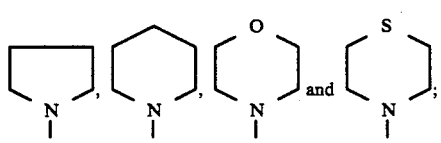

wherein each $L^1$ and $L^2$ is the same or different and is each independently selected from indole moieties (J1) through (J4) ($L^1$ need not be the same as $L^2$)

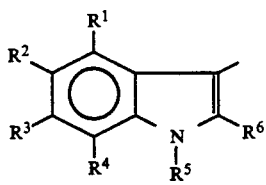 (J1)

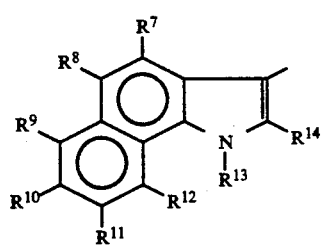 (J2)

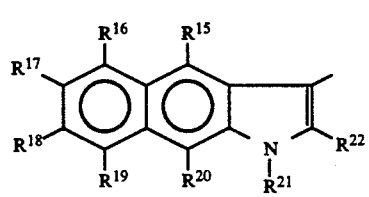 (J3)

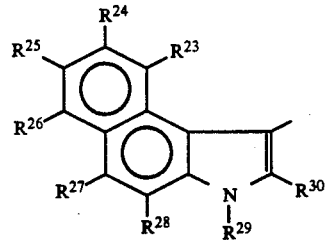 (J4)

wherein in (J1) through (J4) above each of $R^5$, $R^6$, $R^{13}$, $R^{14}$, $R^{21}$, $R^{22}$, $R^{29}$ and $R^{30}$ need not be the same and is each independently selected from hydrogen, alkyl ($C_1$-$C_8$), cycloalkyl, alkoxyalkyl, aroxyalkyl, substituted or unsubstituted aryl such as phenyl, naphthyl or heterocyclyl;

each of $R^1$, $R^2$, $R^3$, $R^4$, $R^7$, $R^8$, $R^9$, $R^{10}$, $R^{11}$, $R^{12}$, $R^{15}$, $R^{16}$, $R^{17}$, $R^{18}$, $R^{19}$, $R^{20}$, $R^{23}$, $R^{24}$, $R^{25}$, $R^{26}$, $R^{27}$ and $R^{28}$ need not be the same and is each independently selected from hydrogen, alkyl ($C_1$-$C_8$), cycloalkyl, substituted or unsubstituted aryl, halogen, alkoxy ($C_1$-$C_8$), aroxy, cycloalkoxy, dialkylamino including symmetrical and unsymmetrical alkyl ($C_1$-$C_8$), alkylcycloalkylamino, dicycloalkylamino, alkylarylamino, diarylamino,

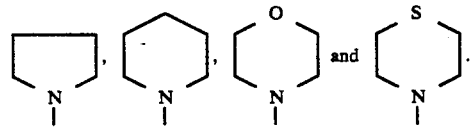

Mono(indolylethylenyl)phthalides (I) were prepared by condensing indolylethylenes (II) with keto acids or their derivatives (III) using condensing agents (IV) [e.g. acid anhydrides, acid chlorides and Lewis acids] in an organic solvent.

Preferred examples of acid anhydrides and acid chlorides are acetic anhydride, propionic anhydride and acetyl chloride. Preferred Lewis acids are zinc chloride, boron trifluoride etherate, zinc chloride/phosphoryl chloride and zinc chloride/thionyl chloride.

Since keto acids or their derivatives (III) undergo ring-chain tautomerism, they contain at least two reactive centers in either open or ring structure. Ring isomers can form derivatives not only from cyclic but also from acyclic structure, depending on the nature of reagents, temperature, solvent and substitution on (III). On the other hand, open or cyclic isomers may yield cyclic derivatives.

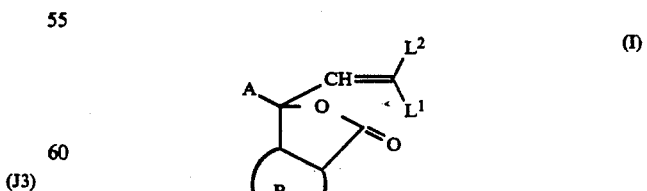 (I)

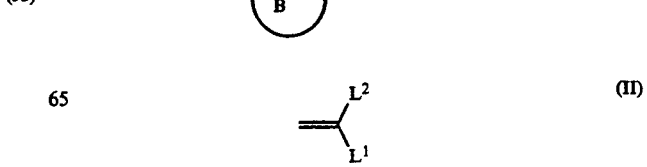 (II)

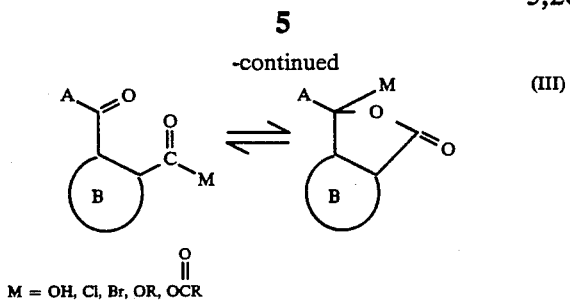

M = OH, Cl, Br, OR, OCR

In the following examples, general procedures for preparing certain mono(indolylethylenyl)phthalides of structure (I) are described; and the examples are not intended to be exhaustive and the moieties, as previously defined, are all eligible for use in any combination in preparing the compounds. Unless otherwise noted, all measurements, percentages and parts are by weight and in the metric system.

Spectroscopic data was used to confirm structures of compounds synthesized.

EXAMPLES

Figure 1:
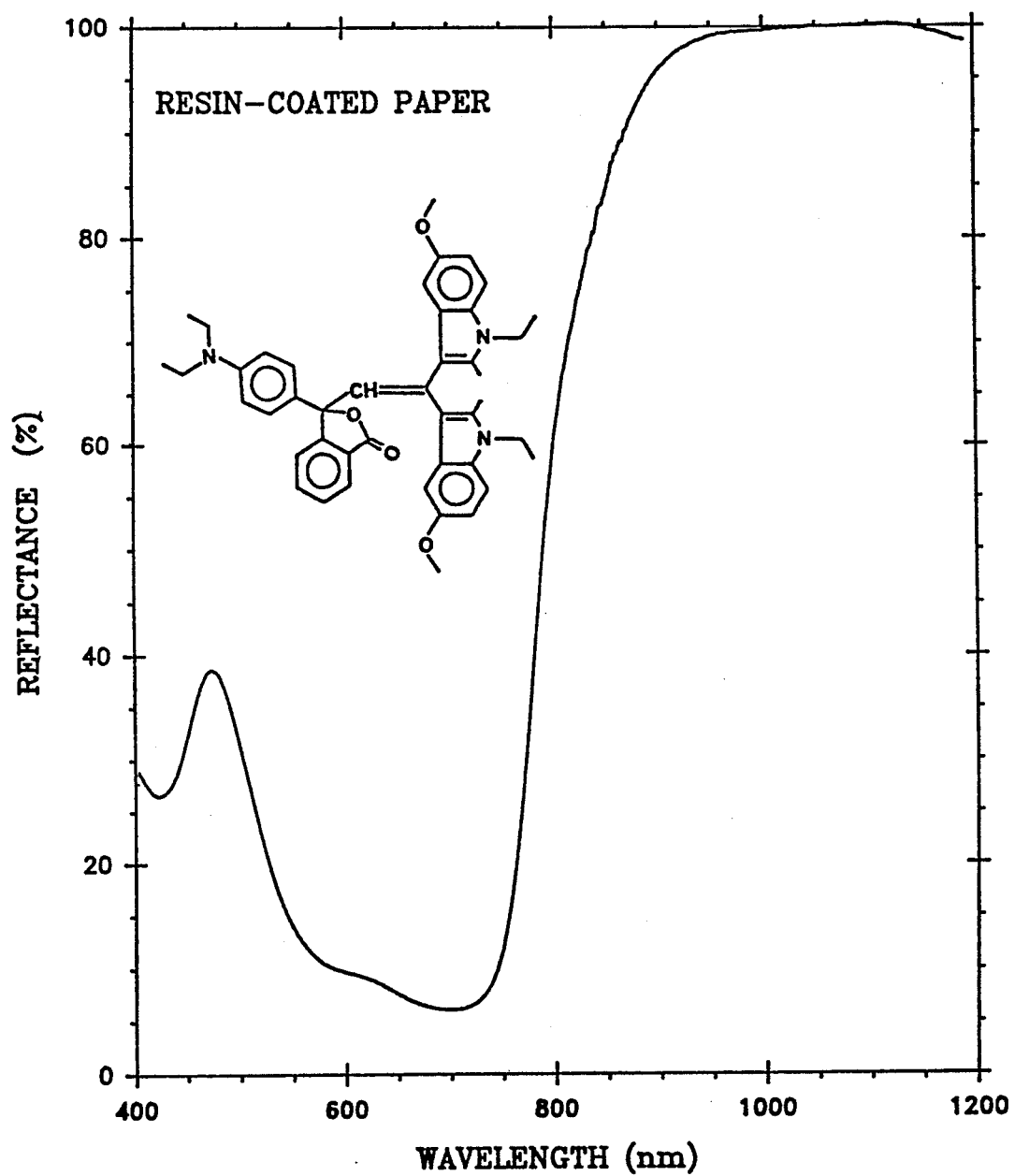
FIG. 1 is a graph of reflectance (%) from 400 to 1200 nm of the following compound when coated on resin-coated paper.

In the following examples, general procedures for preparing certain mono(indolylethylenyl)phthalides of structure (I) are described; and the examples are not intended to be exhaustive and the moieties, as previously defined, are all eligible for use in any combination in preparing the compounds. Unless otherwise noted, all measurements, percentages and parts are by weight and in the metric system. In Table 1, "sh" refers to a shoulder in the absorption spectra. As an illustration, in FIG. 1 there is a shoulder at 570 nm.

Satisfactory spectroscopic data were obtained for new compounds synthesized.

EXAMPLE 1

Preparation of
3-[1,1-bis(1-ethyl-5-methoxy-2-methylindole-3-yl)-ethylene-2-yl]-3-(4-diethylaminophenyl)phthalide

TABLE 1, ENTRY 1

2-(4-Diethylaminobenzoyl)benzoic acid (3.0 g, 0.01 mole) and 1,1-bis(1-ethyl-5-methoxy-2-methylindole-3-yl)ethylene (4.0 g, 0.01 mole) in 1,2-dichloroethane (20 ml) and acetic anhydride (20 ml) were heated at 100° C. (oil bath temperature) for 4 hours. The reaction mixture was cooled to room temperature; treated with ice, toluene and aqueous sodium hydroxide(10%); stirred at 60° C. for 30 minutes; toluene layer separated and the aqueous layer extracted twice with toluene. The toluene extracts were combined, washed twice with hot water, dried and concentrated. The residue was chromatographed on silica gel using toluene and toluene:acetone:: 4:1 as eluants. Fractions containing the blue band were collected, combined and concentrated. The residue was recrystallized from 1,2-dichloroethane/methanol. The product was obtained as a white solid, m.p.: 217°–219° C.; Yield: 5.5 g (81%).

A solution of this product gives a blue color to paper coated with a phenolic resin, with reflectance minima at 570(shoulder) and 703 nm; and a royal blue color to paper coated with silton clay, with reflectance minima as a broad band from 550 to 750 nm.

The calculated analysis for $C_{44}H_{47}N_3O_4$, the title compound, is C, 77.50%; H, 6.95%; N, 6.16%; and O, 9.39%. Found on analysis: C, 77.04%; H, 7.12%; and N, 5.97%.

EXAMPLE 2

Preparation of
3-[1,1-bis(1-ethyl-2-methylindole-3-yl)ethylene-2-yl]-3-(4-diethylaminophenyl)phthalide

TABLE 1, ENTRY 2

2-(4-Diethylaminobenzoyl)benzoic acid (3.0 g, 0.01 mole) and 1,1-bis(1-ethyl-2-methylindole-3-yl)ethylene (3.4 g, 0.01 mole) in 1,2-dichloroethane (20 ml) and boron trifluoride etherate (2 ml, 2.3 g, 0.016 mole) were heated (oil bath temperature 100° C.) with exclusion of moisture. After 10 hours, the reaction mixture was cooled to room temperature, stirred with dilute ammonium hydroxide and toluene for 10 minutes at 60° C. and the organic layer separated. The organic layer was washed with hot water, dried and concentrated and the resulting residue chromatographed on silica gel using toluene and toluene:acetone::4:1 as eluants. Fractions containing the blue band were collected, combined and concentrated and the residue was further purified by medium pressure liquid chromatography on silica gel. After recrystallization from toluene/hexane, the product was obtained as a pale yellow solid, m.p.: 124°–126° C. Yield: 4.5 g (72%).

A solution of the product gives a blue color to paper coated with a phenolic resin, with reflectance minima at 570(shoulder) and 710 nm; and a royal blue color to paper coated with silton clay, with reflectance minima as a broad band from 550 to 750 nm.

The calculated analysis for $C_{42}H_{43}N_3O_2$, the title compound, is C, 81.13%; H, 6.97%; N, 6.76%; and O, 5.15%. Found on analysis: C, 80.81%; H, 7.27%; and N, 6.80%.

EXAMPLE 3

Preparation of
3-[1-(5-chloro-2,7-dimethyl-1-ethylindole-3-yl)-1-(1-ethyl-2,5,7-trimethylindole-3-yl)ethylene-2-yl]-3-(4-diethylaminophenyl)-6-dimethylaminophthalide

TABLE 1, ENTRY 3

2-(4-Diethylaminobenzoyl)-5-dimethylaminobenzoic acid (1.9 g,5.5 mmole) and 1-(5-chloro-2,7-dimethyl-1-ethylindole-3-yl)-1-(1-ethyl-2,5,7-trimethylindole-3-yl)ethylene (2.3 g,5.5 mmole) were mixed with glacial acetic acid (25 ml) and concentrated sulfuric acid (0.6 g,5.9 mmole) and the reaction mixture was stirred at 40° C. for 24 hours with exclusion of moisture. Then, the reaction mixture was cooled to room temperature and poured into excess aqueous sodium hydroxide (10%) and toluene (200 ml). After stirring at 40° C. for 30 minutes, the toluene layer was separated, washed with hot water, dried and concentrated. The residue was purified by column chromatography (silica gel), followed by medium pressure liquid chromatography on silica gel. After recrystallization from toluene/methanol the product was obtained as a bluish white solid, m.p.: 190°–193° C. Yield: 1.3 g (32%).

A solution of this product gives a blue color to paper coated with a phenolic resin, with reflectance minima at 540 (shoulder) and 719 nm; and a blue color to paper coated with silton clay, with reflectance minima at 647 and 700 (shoulder) nm.

The calculated analysis for $C_{47}H_{53}N_4O_2Cl$, the title compound, is C, 76.14%; H, 7.21%; N, 7.56%; O, 4.32%; and Cl, 4.78%. Found on analysis: C, 75.77%; H, 7.16%; N, 7.63%; and Cl, 4.93%.

EXAMPLE 4

Preparation of
3-[1,1-bis(1-ethyl-2-methylindole-3-yl)ethylene-2-yl]-3-(4-dimethylaminophenyl)-4,5,6,7-tetrachlorophthalide

TABLE 1, ENTRY 6

3-Acetoxy-3-(4-dimethylaminophenyl)-4,5,6,7-tetrachlorophthalide (4.5 g, 0.01 mole), 1,1-bis(1-ethyl-2-methylindole-3-yl)ethylene (3.4 g, 0.01 mole) and zinc chloride (1.4 g, 0.01 mole) in 1,2-dichloroethane (40 ml) were refluxed with stirring in a moisture free atmosphere. After 10 hours, the reaction mixture was worked up as described in EXAMPLE 1. The crude product was heated in hexane and filtered. Yield: 3.2 g (44%), pale yellow solid, m.p.: 211°–213° C.

A solution of the product gives a bluish green color to paper coated with a phenolic resin, with reflectance minima at 600 (shoulder) and 719 nm; and a royal blue color to paper coated with silton clay, with reflectance minima at 600 and 720(shoulder) nm.

The calculated analysis for $C_{40}H_{35}N_3O_2Cl_4$, the title compound, is C, 65.67%; H, 4.82%; N, 5.74%; O, 4.37%; and Cl, 19.39%. Found on analysis: C, 65.60%; H, 5.10%; N, 5.58%; and Cl, 19.66%.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes can be made by those skilled in the art without departing from the spirit and scope of the invention.

TABLE 1

REFLECTANCE MINIMA AND COLOR OF MONO(INDOLYLETHYLENYL)-PHTHALIDES ON RESIN-COATED AND SILTON-COATED PAPERS

| ENTRY | COMPOUND | REFLECTANCE MINIMA (nm)* AND COLOR ON | |
|---|---|---|---|
| | | RESIN-COATED | SILTON-COATED |
| 1. | (structure) | 570 (Sh) 703 Blue | 550–750 Broad Band Royal Blue |
| 2. | (structure) | 570 (Sh) 710 Blue | 550–750 Broad Band Royal Blue |
| 3. | (structure) | 540 (Sh) 719 Blue | 647 700 (Sh) Blue |
| 4. | (structure) | 570 682 825 (Sh) Bluish Green | 572 700 (Sh) Purple |

TABLE 1-continued

REFLECTANCE MINIMA AND COLOR OF MONO(INDOLYLETHYLENYL)-
PHTHALIDES ON RESIN-COATED AND SILTON-COATED PAPERS

| | | REFLECTANCE MINIMA (nm)* AND COLOR ON | |
|---|---|---|---|
| ENTRY | COMPOUND | RESIN-COATED | SILTON-COATED |
| 5. | | 565<br>702<br>Greyish Blue | 570<br>698<br>Blue |
| 6. | | 600 (Sh)<br>719<br>Green | 600<br>720 (Sh)<br>Blue |
| 7. | | 620 (Sh)<br>713<br>Bluish Green | 600<br>690 (Sh)<br>Blue |
| 8. | | 610 (Sh)<br>690 (Sh)<br>762<br>Bluish Green | 620 (Sh)<br>700 (Sh)<br>758<br>Pale Green |
| 9. | | 590 (Sh)<br>740<br>Pale Blue | 600 (Sh)<br>741<br>Greenish Blue |

TABLE 1-continued
REFLECTANCE MINIMA AND COLOR OF MONO(INDOLYLETHYLENYL)-
PHTHALIDES ON RESIN-COATED AND SILTON-COATED PAPERS

| ENTRY | COMPOUND | REFLECTANCE MINIMA (nm)* AND COLOR ON | |
|---|---|---|---|
| | | RESIN-COATED | SILTON-COATED |
| 10. | | 610 (Sh) 720 Green | 600 (Sh) 696 Green |

*Only the reflectance minima above 500 nm are reported.
Sh = Shoulder, ⌽ = Phenyl

What is claimed is:

1. A mono(indolylethylenyl)phthalide of the formula:

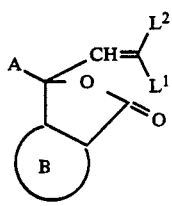

wherein A is independently selected from

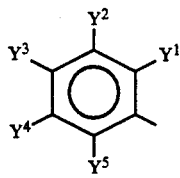

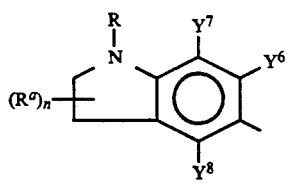

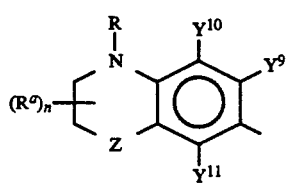

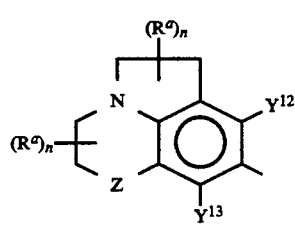

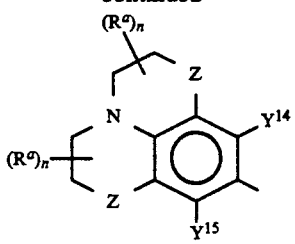

wherein $Y^3$ is independently selected from dialkylamino consisting of symmetrical and unsymmetrical alkyl ($C_1$-$C_8$), alkylcycloalkylamino, dicycloalkylamino, alkylarylamino, diarylamino, dialkoxyalkylamino,

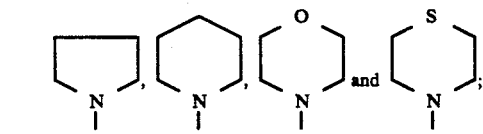

wherein each of $Y^1$, $Y^2$, $Y^4$-$Y^{15}$ is the same as $Y^3$ or independently selected from hydrogen, alkyl ($C_1$-$C_8$), alkoxy ($C_1$-$C_8$) and halogen;

wherein R is independently selected from alkyl ($C_1$-$C_8$), alkoxyalkyl, and aryl (substituted or unsubstituted);

wherein Z is independently selected from $CH_2$, O, S, $SO_2$ or NR;

wherein each $R^a$ is independently selected from alkyl ($C_1$-$C_8$) and hydrogen;

wherein each n is an integer selected from 0 to four;

wherein B is independently selected from

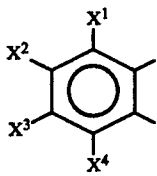

wherein each of $X^1$-$X^4$ is independently selected from hydrogen, halogen, alkyl ($C_1$-$C_8$), alkoxy ($C_1$-$C_8$), dialkylamino consisting of symmetrical and unsymmetrical alkyl ($C_1$-$C_8$), alkylcycloalkylamino, dicycloalkylamino, alkylarylamino, diarylamino,

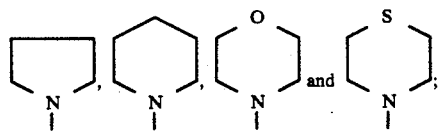

wherein each $L^1$ and $L^2$ is the same or different and is each independently selected from indole moieties (J1) through (J4)

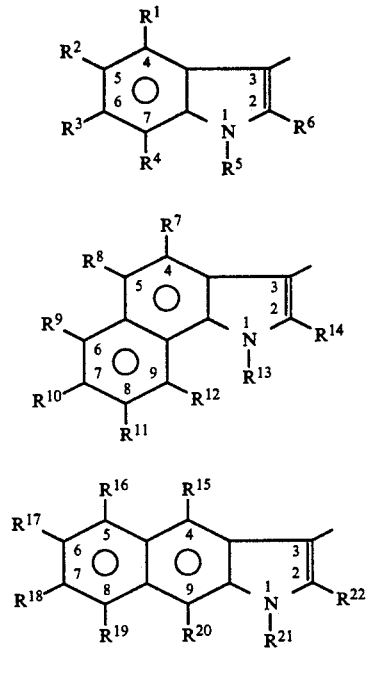

wherein in (J1) through (J4) above each of $R^5$, $R^6$, $R^{13}$, $R^{14}$, $R^{21}$, $R^{22}$, $R^{29}$ and $R^{30}$ need not be the same and is each independently selected from hydrogen, alkyl ($C_1$–$C_8$), cycloalkyl, alkoxyalkyl, aroxyalkyl, substituted or unsubstituted aryl
each of $R^1$, $R^2$, $R^3$, $R^4$, $R^7$, $R^8$, $R^9$, $R^{10}$, $R^{11}$, $R^{12}$, $R^{15}$, $R^{16}$, $R^{17}$, $R^{18}$, $R^{19}$, $R^{20}$, $R^{23}$, $R^{24}$, $R^{25}$, $R^{26}$, $R^{27}$ and $R^{28}$ need not be the same and is each independently selected from hydrogen, alkyl ($C_1$–$C_8$), cycloalkyl, substituted or unsubstituted aryl, halogen, alkoxy ($C_1$–$C_8$), aroxy, cycloalkoxy, dialkylamino consisting of symmetrical and unsymmetrical alkyl ($C_1$–$C_8$), alkylcycloalkylamino, dicycloalkylamino, alkylarylamino, diarylamino,

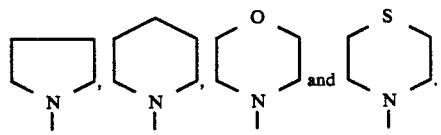

2. The compound according to claim 1 wherein the mono(indolylethylenyl)phthalide is:

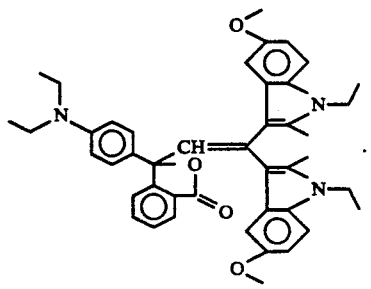

3. The compound according to claim 1 wherein the mono(indolylethylenyl)phthalide is:

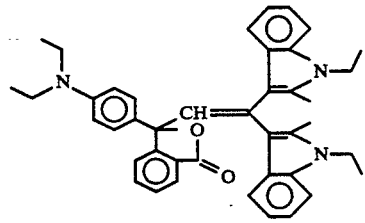

4. The compound according to claim 1 wherein the mono(indolylethylenyl)phthalide is:

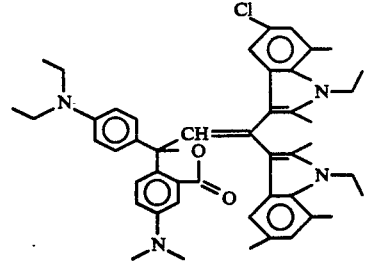

5. The compound according to claim 1 wherein the mono(indolylethylenyl)phthalide is:

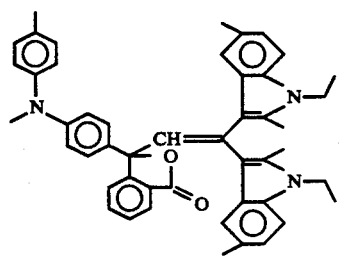

6. The compound according to claim 1 wherein the mono(indolylethylenyl)phthalide is:

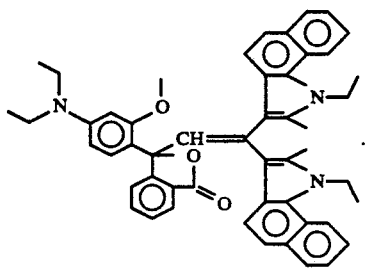

7. The compound according to claim 1 wherein the mono(indolylethylenyl)phthalide is:

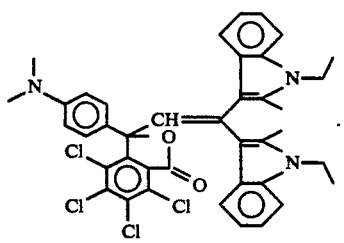

8. The compound according to claim 1 wherein the mono(indolylethylenyl)phthalide is:

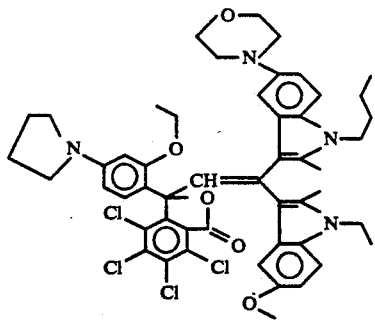

9. The compound according to claim 1 wherein the mono(indolylethylenyl)phthalide is:

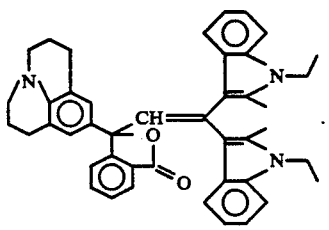

10. The compound according to claim 1 wherein the mono(indolylethylenyl)phthalide is:

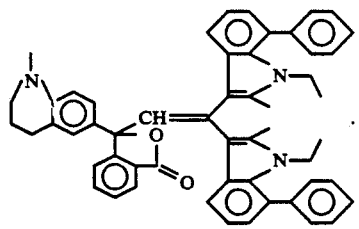

11. The compound according to claim 1 wherein the mono(indolylethylenyl)phthalide is:

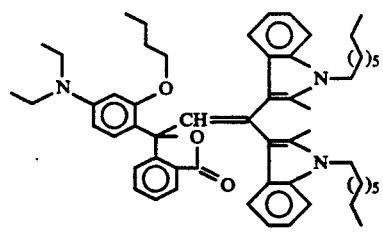

* * * * *